United States Patent
Nakatani et al.

(10) Patent No.: US 7,608,417 B2
(45) Date of Patent: Oct. 27, 2009

(54) CELL ELECTRO-PHYSIOLOGICAL SENSOR AND METHOD OF MANUFACTURING THE SAME

(75) Inventors: Masaya Nakatani, Hyogo (JP); Hiroshi Ushio, Hyogo (JP); Soichiro Hiraoka, Osaka (JP); Abdellah Menikh, Tustin, CA (US)

(73) Assignee: Panasonic Corporation, Osaka (JP)

( * ) Notice: Subject to any disclaimer, the term of this patent is extended or adjusted under 35 U.S.C. 154(b) by 464 days.

(21) Appl. No.: 11/272,892

(22) Filed: Nov. 14, 2005

(65) Prior Publication Data

US 2007/0108478 A1    May 17, 2007

(51) Int. Cl.
*C12Q 1/02*    (2006.01)
(52) U.S. Cl. .......................... 435/29; 435/63; 435/287.1
(58) Field of Classification Search .................... 435/29, 435/63, 287.1
See application file for complete search history.

(56) References Cited

U.S. PATENT DOCUMENTS

| | | | |
|---|---|---|---|
| 6,338,877 B1 * | 1/2002 | Kamei et al. ................ | 427/444 |
| 2002/0195197 A1 * | 12/2002 | Egitto et al. ................ | 156/327 |
| 2003/0113833 A1 | 6/2003 | Oka et al. | |

FOREIGN PATENT DOCUMENTS

| | | |
|---|---|---|
| JP | P2002-518678 | 6/2002 |
| WO | WO 01/48474 A1 | 7/2001 |
| WO | WO 02/055653 | 7/2002 |
| WO | WO 2004/018690 A1 | 3/2004 |

OTHER PUBLICATIONS

International Search Report for PCT/JP2006/310597, dated Oct. 6, 2006.
T. Sordel et al., "A Silicon-Based Multi-Patch Device: Application for Ionic Currents Sensoring on Single Cells", 8th International Conference on Miniaturized Systems for Chemistry and Life Sciences, Sep. 26-30, 2004, pp. 521-523, Malmo, Sweden.

* cited by examiner

Primary Examiner—Michael B Shingleton
(74) Attorney, Agent, or Firm—RatnerPrestia

(57) ABSTRACT

A cell electro-physiological sensor includes a sensor chip including a partition board having a first surface and a second surface opposite to the first surface, a member for forming a first region provided on the first surface of the partition board, and a member for forming a second region provided on the second surface of the partition board. The partition board has a through-hole provided therein, the through-hole having a first opening which opens to the first surface, a second opening which opens to the second surface, and a wall. The first region contacts the first opening of the through-hole. The first region is arranged to contain cell suspension. The atomic ratio of carbon at the first surface of the partition board is not greater than 15 atomic percent of the composition of the first surface. The cell electro-physiological sensor causes the cell to be tightly held at the first opening of the through-hole in the partition board, thereby measuring a potential of the cell efficiently.

20 Claims, 9 Drawing Sheets

Fig. 13

| | Contact Angle D1 (deg.) | Atomic Ratio | | |
|---|---|---|---|---|
| | | Si | O | C |
| Sample S1 | 49.5 | 0.56 | 0.26 | 0.18 |
| Sample S2 | 7.8 | 0.58 | 0.28 | 0.14 |
| Sample S3 | 3.1 | 0.63 | 0.28 | 0.09 |

US 7,608,417 B2

CELL ELECTRO-PHYSIOLOGICAL SENSOR AND METHOD OF MANUFACTURING THE SAME

FIELD OF THE INVENTION

The present invention relates to a cell electro-physiological sensor for measuring a cell electro-physiological phenomenon, such as an intracellular potential or an extracellular potential, to examine a physicochemical change in an activity in a cell, and relates to a method of manufacturing the sensor.

BACKGROUND OF THE INVENTION

A patch-clamp method in electrophysiology is known as the "gold standard" method for measuring ion channel activity in cell membrane. Ion channels have crucial roles in physiology and pathophysiology and are important drug targets. Patch clamping has rapidly become the "gold standard" in studying ion channel function but is still a laborious process requiring precision micromanipulation under high power visual magnification, vibration dumping, and an experienced and skilful experimenter, thus having been judged unfavorable for high throughput recording. In recent developments, the application of microstructured chips for patch clamping has been put forward, the common patch pipette is replaced by a microfabricated chip that enable the positioning and sealing of cells via an automated suction protocols.

Planar probes utilizing processing technologies are proposed. Such probes are applicable to an automated system which does not require the inserting of a micro pipette into a cell.

Japanese Patent Laid-Open Publication No. 2003-527581 discloses a device for electrically measuring an object in a medium. In this device, the object seals an orifice, thereby providing first and second cavities insulated electrically from each other. Then, the device measures the object electrically in the medium based on an impedance between electrodes located in the first and second cavities, respectively.

International Application Publication No. WO02/055653 discloses a technique of measuring an extracellular potential with a cell electro-physiological sensor which includes wells provided in a substrate with cell holders, measuring electrodes for measuring an electrical signal at each well, and reference electrodes.

"Micro Total Analysis Systems 2004", pp. 521-522, T. Sordel et al (2004) discloses a technology for tightly holding an HEK293 cell, which is a human cultured cell in a hole having a diameter of 2.5 µm in a layer made of $SiO_2$, and for measuring an extracellular potential.

A through-hole provided in a planar substrate functions as a tip opening of a glass pipette. This hole allows electro-physiological phenomenon of cells to be recorded precisely while the cells are automatically pulled and easily held by a suction force from a back surface of the substrate. It is important for the measuring of the cells with a small background noise that the cells are securely held in the planar substrate of a device.

However, none of the above prior arts describes an optimum structure of the planar substrate, such as its shape and its surface condition, which affects holding properties of the cells.

SUMMARY OF THE INVENTION

A cell electro-physiological sensor includes a sensor chip including a partition board having a first surface and a second surface opposite to the first surface, a first region provided on the first surface of the partition board, and a second region provided on the second surface of the partition board. The partition board has a through-hole provided therein, the though-hole having a first opening which opens to the first surface, a second opening which opens to the second surface, and a wall. The first region contacts the first opening of the through-hole. The first region is arranged to hold cell suspension. The second region contacts the second opening of the through-hole. The atomic ratio of carbon at the first surface of the partition board is not greater than 15 atomic percent of the composition of the first surface of the partition board.

The cell electro-physiological sensor causes the cell to be tightly held at the first opening of the through-hole in the partition board, thereby measuring a potential of the cell efficiently.

BRIEF DESCRIPTION OF THE DRAWINGS

FIG. 13 is a table showing an evaluation result of the cell electro-physiological sensor according to the embodiment.

DETAILED DESCRIPTION OF THE PREFERRED EMBODIMENT

Figure 1:
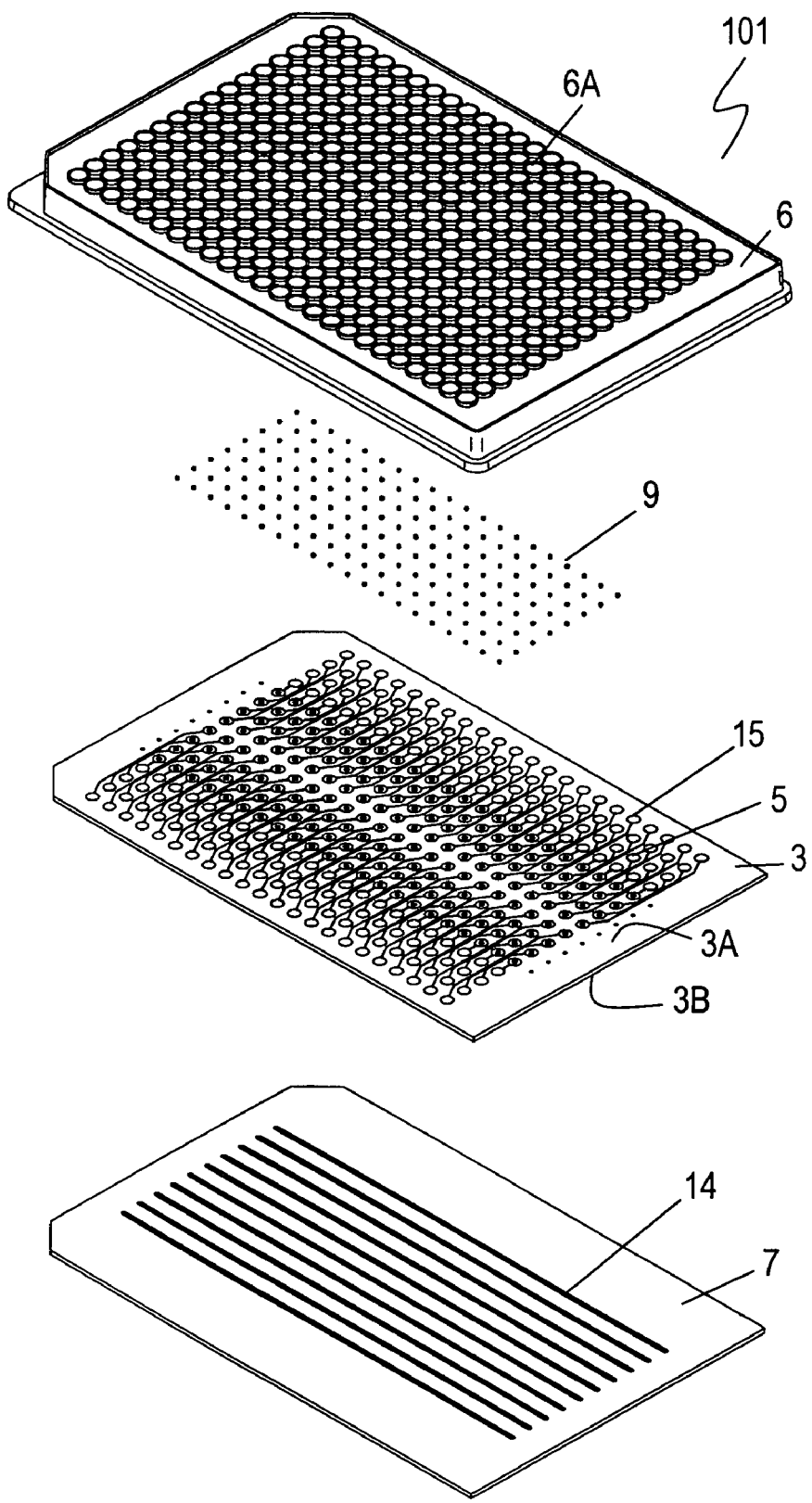
FIG. 1 is an exploded perspective view of a cell electro-physiological sensor according to an exemplary embodiment of the present invention.
Figure 2:
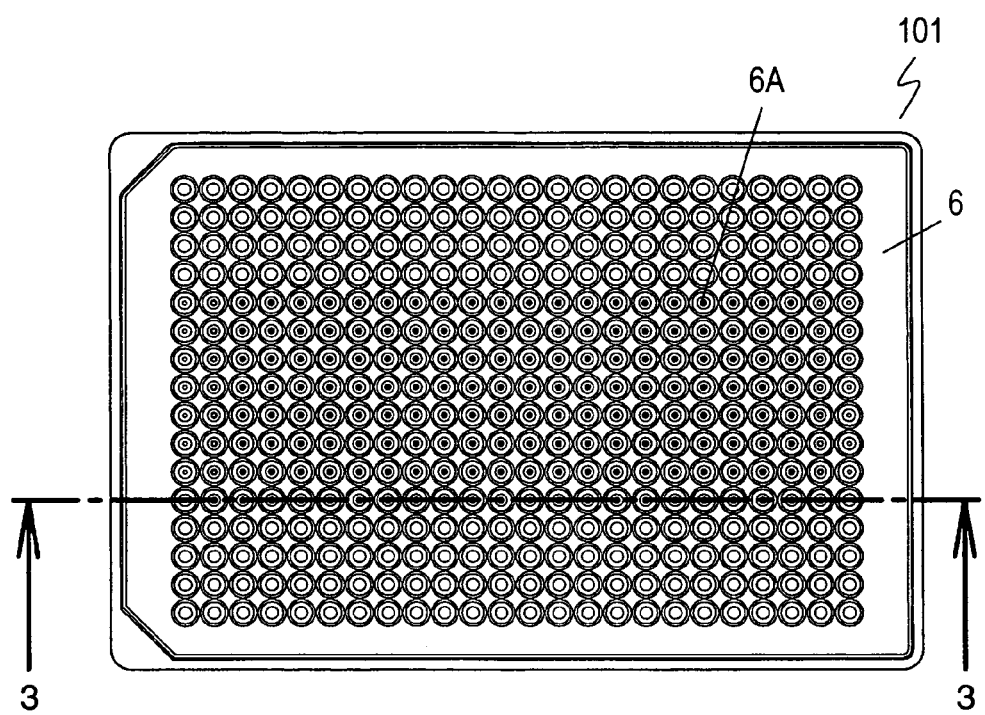
FIG. 2 is an upper view of the cell electro-physiological sensor according to the embodiment.
Figure 3:
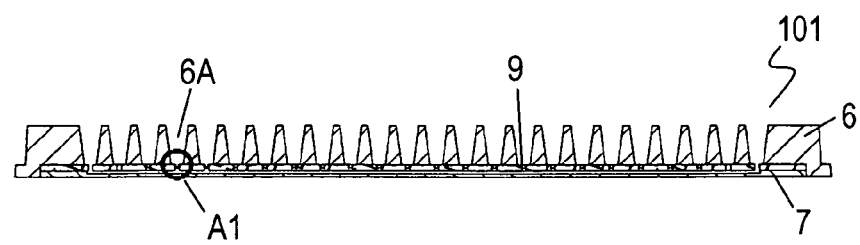
FIG. 3 is a cross sectional view of the cell electro-physiological sensor shown in FIG. 2 at line 3-3.
Figure 4:
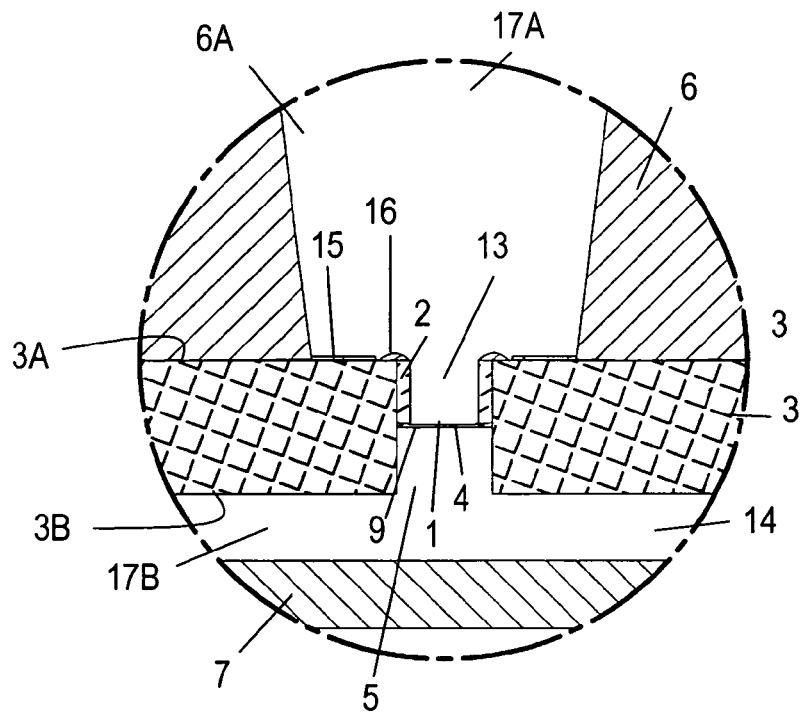
FIG. 4 is an enlarged cross sectional view of the cell electro-physiological sensor according to the embodiment.
Figure 5:
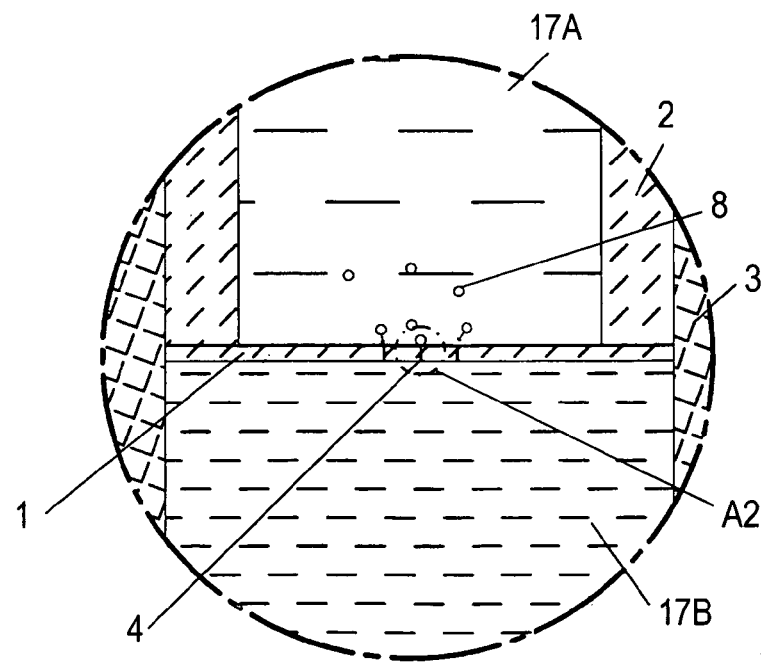
FIG. 5 is an enlarged cross sectional view of the cell electro-physiological sensor according to the embodiment.
Figure 6:
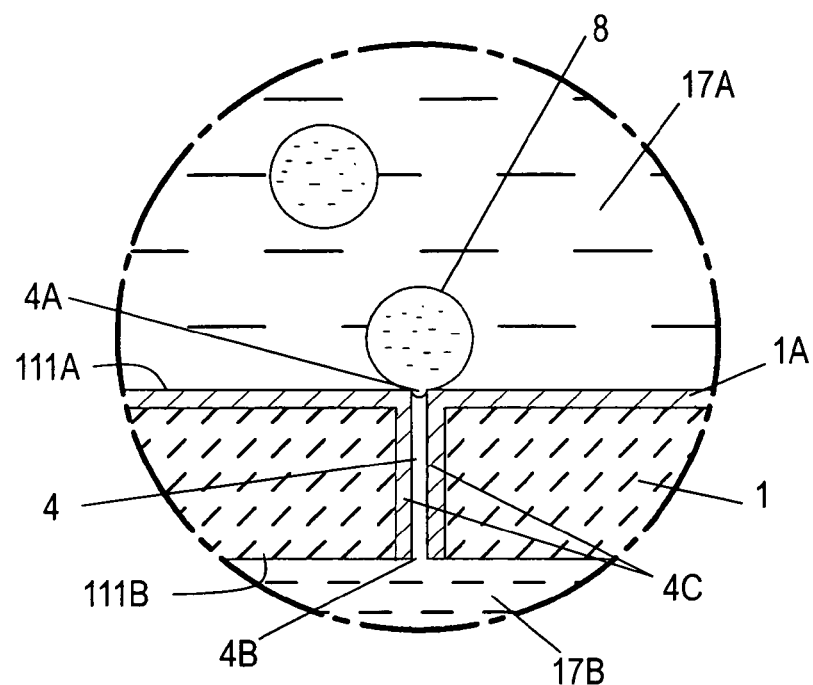
FIG. 6 is an enlarged cross sectional view of the cell electro-physiological sensor according to the embodiment.

FIG. 1 is an exploded perspective view of a cell electro-physiological sensor 101 according to an exemplary embodiment of the present invention. FIG. 2 is an upper view of the cell electro-physiological sensor 101. FIG. 3 is a cross sectional view of the cell electro-physiological sensor 101 at line 3-3 shown in FIG. 2. FIG. 4 is an enlarged cross sectional view of a portion A1 of the cell electro-physiological sensor 101 shown in FIG. 3. FIG. 5 is an enlarged cross sectional view of the cell electro-physiological sensor 101. FIG. 6 is an enlarged cross sectional view of a portion A2 of the cell electro-physiological sensor 101 shown in FIG. 5. The cell electro-physiological sensor 101 includes sensor chips 9, a chip plate 3 having the sensor chips 9 embedded therein, a well plate 6, and a passage plate 7. The well plate 6 and the passage plate 7 contact an upper surface 3A and an lower surface 3B of the chip plate 3, respectively. As shown in FIG. 4, the sensor chip 9 includes a partition board 1 made of a rigid material, such as a silicon plate, having an insulating layer 1A of insulating material, such as silicon dioxide, and a frame 2 mounted on the outside edge of the partition board 1. The chip plate 3 has through-holes 5 therein extending between the upper surface 3A and the lower surface 3B. The sensor chip 9 is inserted in each through-hole 5 with an adhesive 16 without any clearance.

The partition board 1, if being made of a silicon substrate, may have the insulating layer 1A at an upper surface thereof The partition board 1, if being made of insulating material, such as glass or silica, does not need the insulating layer 1A.

The well plate 6 has wells 6A therein to communicate with through-holes 5 in the partition board 1, respectively. The passage plate 7 has a passages 14 provided in the upper surface 7A of the plate 7 for allowing a culture solution to flow. The upper surface 7A of the passage plate 7 contacts the lower surface 3B of the chip plate 3, thus allowing it's the passages 14 to communicate with the through-holes 5, respectively. This arrangement defines regions 17A and 17B separated by the partition board 1 in the cell electro-physiological sensor 101. The region 17A extends between an upper surface 111A of the partition board 1 and the well 6A. The partition board 1, the chip plate 3, and the well 6A function as a member for forming the region 17A. The region 17B extends between a lower surface 111B of the partition board 1 and the passage 14. The partition board 1, the chip plate 3, and the passage plate 7 function as a member form forming the region 17B. The regions 17A and 17B may hold kinds of solution different from each other. The region 17A contacts an opening 4A of through-hole 4 provided in the partition board 1 while the region 17B contacts an opening 4B of the through-hole 4.

Electrode 15 made of metallic material, such as Pt, Au, Ag, or Cl, are mounted on the upper surface 3A of the chip plate 3 and around the through-hole 5.

The partition board 1 has the through-hole 4 therein which allows the regions 17A and 17B to communicate with each other, and has the openings 4A and 4B opening to the regions 17A and 17B, respectively. As shown in FIGS. 5 and 6, the region 17A holds solution containing cells 8, i.e., cell suspension. When the solution is sucked via the through-holes 4 from the region 17B, the cells 8 move towards the openings 4A of the through holes 4, and then are held at the openings 4A. The through-holes 4 have sizes determined to be smaller than those of the cells 8.

The cell 8 is held in the region 17A by the sucking from the region 17B. At this moment, the cell 8 deforms at the opening 4A of the through-hole 4, and a portion of its cell membrane contacts a wall 4C of the through-hole 4 and the upper surface 111A of the partition board 1, as shown in FIG. 6. In the cell electro-physiological sensor 101, the walls 4C of the through-holes 4 and the upper surface 111A of the partition board 1 are covered with an insulating layer 1A made of insulating material, such as silicon dioxide. The atomic ratio of carbon in a cell contact surface, i.e., the wall 4C and the upper surface 111A of the partition board 1 which contact the cell 8, is set to be smaller than 15 atomic percent of the composition of the surface. According to the embodiment, the atomic ratio of carbon is measured by an X-ray photo-electron spectroscopy (XPS) technique. The XPS technique involves the measuring of the energy and the number of photo-electrons as to specify the number of atoms and the environment about the atoms on and near the surface, and thus to detect a chemical bonding of the atoms. More particularly, the name, the number, and the chemical condition of atoms are detected by exposing the surface of the partition board 1 to X-ray and measuring the photo-electrons excited by the X-ray. According to the embodiment, a spot diameter of the X-ray is set to about 100 µm. While the surface of the partition board 1 exposes to X-ray perpendicularly perpendicular to the surface, the photo-electrons are measured from an angle of 45 degrees to the surface. Each atom staying at a depth of about 20 nm from the surface is detected. In other words, the number of atoms or molecules on the contact surface is the number of atoms existing from the surface to a depth of 20 nm.

According to the present embodiment, a cellular potential as a cell electro-physiological phenomenon is measured, however it is not limited. Other cell electro-physiological phenomena, such as a membrane current flowing on a cell membrane, a membrane resistance, and a membrane capacitance, are often measured in order to measure characteristics of ion channels.

Since the outer surface of the cell membrane is a complex mixture of various carbohydrates, proteins, and lipids in which a numerous hydroxyl groups were present, variety of ions and molecules are adhered to the surface of the sensor during manufacturing the sensor. Among those many organic compounds block making hydrogen bonds between cell membrane and the surface of the sensor. Therefore, reducing organic compounds from the surface of the partition board 1 and creating OH groups on the surface improve dramatically the interaction between the cell membrane and the surface of the sensor, thereby allowing a cellular potential to be measured accurately and quickly.

Figure 7:
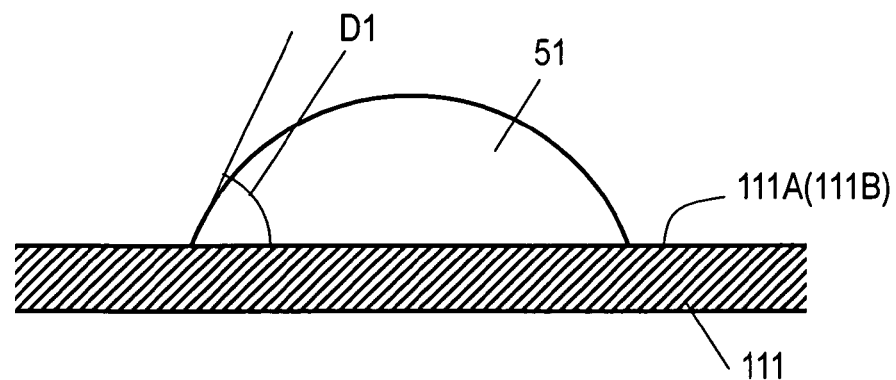
FIG. 7 illustrates hydrophilicity of a partition board of the cell electro-physiological sensor according to the embodiment.

Controlling hydrophilicity of the partition board 1 is effective to increase an affinity of the surface of the partition board 1 for the culture solution, extracellular solution, or intracellular solution. FIG. 7 shows the hydrophilicity of the partition board 1. A water drop 51 of double distilled water is provided on the surface of the partition board 1. A contact angle D1 of the water drop 51 on the surface is preferably not greater than 10 degrees. This condition is necessary but not sufficient.

In the cell electro-physiological sensor 101, the atomic ratio of carbon in the surface of the partition board 1 is reduced, and active hydroxyl groups are generated for the purpose of increasing hydrogen bonds between cell membrane and the surface, thus preventing the leakage of an electric current between the regions 17A and 17B. This allows the cell potential to be measured under a small background noise. The upper surface 111A, the cell contact surface, of the partition board 1 contacting the cells 8 has the hydrophilicity, allows the culture solution, the extracellular solution, or the intracellular solution together with the cells 8 to flow into the through-holes 4 easily. As the solution is sucked from the region 17B and flows into the region 17B, the cells 8 are held at the openings 4A of the through-holes 4 and on the surface 111A, and have the cell potentials to be measured easily. The hydrophilicity of the inner walls 4C of the through holes 4 and the lower surface 111B of the partition board 1 is preferably increased as well as of the upper surface 111A of the partition board 1.

The larger the hydrophilicity of the walls 4C of the through-holes 4 of the partition board 1 is, the more the foregoing effect is provided.

A method for removing organic compounds from the cell contact surface, the upper surface 111A of the partition board 1, to achieve the atomic ratio of carbon not greater than 15 atomic percent of the composition of the surface, and a method for increasing the hydrophilicity of the upper surface 111A, the lower surface 111B, and the inner walls 4C of the through holes 4 of the partition board 1 in the cell electro-physiological sensor 101 will be described in detail below.

First, a method of manufacturing the cell electro-physiological sensor 101 will be explained.

FIGS. 8 to 15 are cross sectional views the cell electro-physiological sensor 101 for illustrating the method of manufacturing the sensor.

Figure 8:
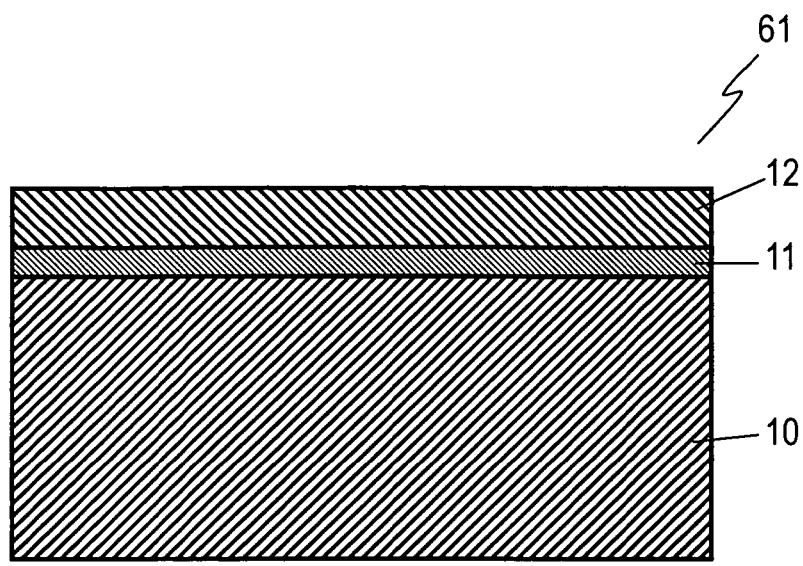
FIG. 8 is a cross sectional view of the cell electro-physiological sensor for illustrating a method of manufacturing the sensor according to the embodiment.

First, as shown in FIG. 8, a laminated substrate 61 including a silicon base 10, a silicon dioxide layer 11 on the silicon base 10, and a thin silicon layer 12 on the silicon dioxide layer 11 is prepared.

Figure 9:
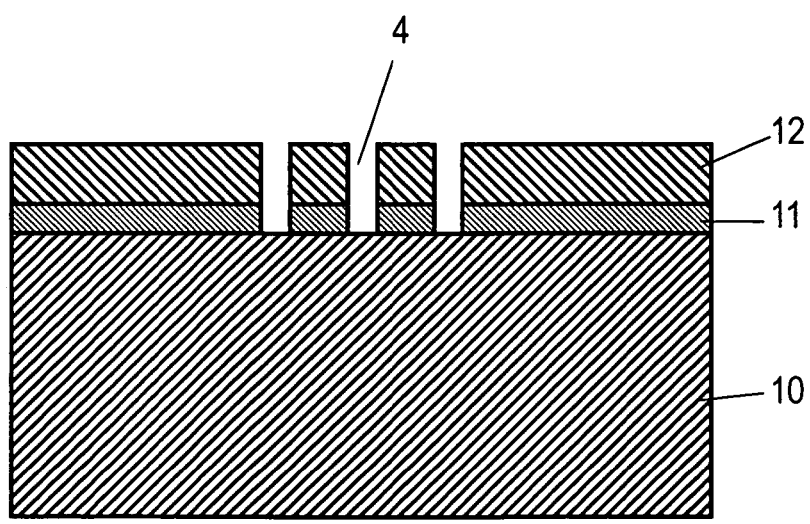
FIG. 9 is a cross sectional view of the cell electro-physiological sensor for illustrating the method of manufacturing the sensor according to the embodiment.

Then, as shown in FIG. 9, a photo-lithography process is applied for providing the through-holes 4 in both the thin silicon layer 12 and the silicon dioxide layer 11.

Figure 10:
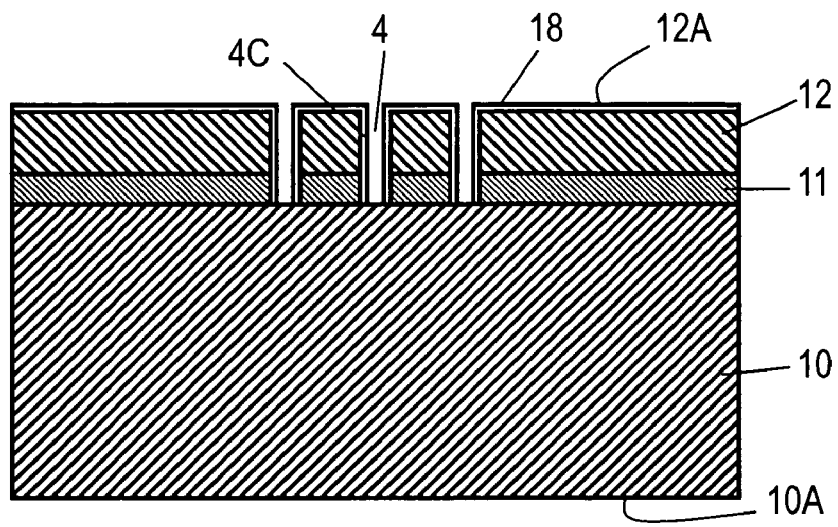
FIG. 10 is a cross sectional view of the cell electro-physiological sensor for illustrating the method of manufacturing the sensor according to the embodiment.

Then, as shown in FIG. 10, a silicon dioxide layer 18 is provided on the upper surface 12A and the walls 4C of the through holes 4 in the thin silicon layer 12. The silicon dioxide layer 18 has a thickness not smaller than 0.3 μm, preferably not smaller than 0.5 μm. The silicon dioxide layer 18 may be deposited preferably by either a thermal oxidation process in which the substrate 61 is heated up to a temperature not lower than 1100° C. under an oxygen atmosphere, a sputtering process for depositing a layer having fine particles under a vacuum condition, or a chemical vapor deposition (CVD) process. The thermal oxidation process causes the silicon dioxide layer 18 to be deposited uniformly on the walls 4C of the through-holes 4 and the upper surface 12A of the thin silicon layer 12. The sputtering process and the CVD process cause the silicon dioxide layer 18 on the walls 4C of the through holes 4 of the thin silicon layer 12 to be thinner than the silicon dioxide layer 18 on the upper surface 12A of the thin silicon layer 12, however, provide a smooth surface of the silicon dioxide layer 18, thus having the hydrophilicity than the layer provided by the thermal oxidation process.

Figure 11:
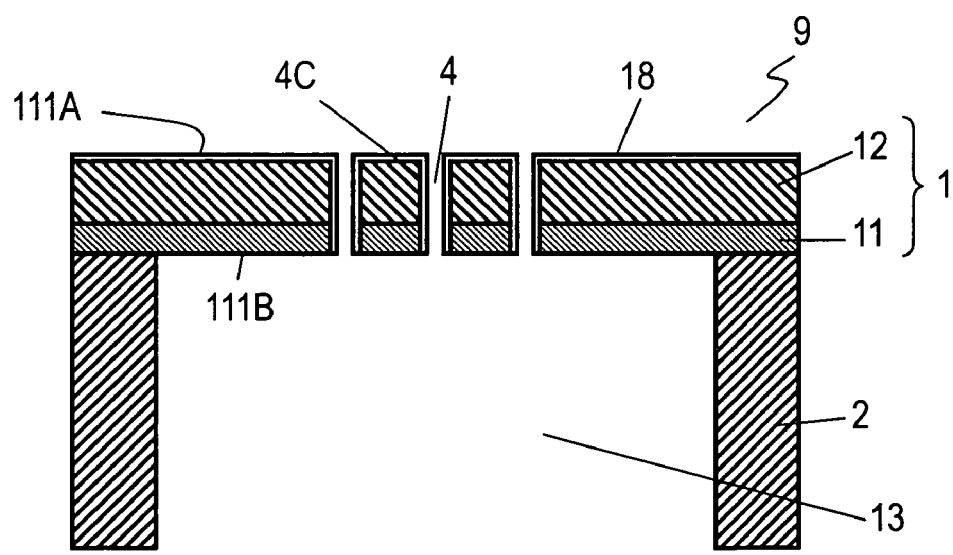
FIG. 11 is a cross sectional view of the cell electro-physiological sensor for illustrating the method of manufacturing the sensor according to the embodiment.

Then, as shown in FIG. 11, a photo-lithography process is applied for providing a cavity 13 in the silicon base 10 extending from the upper surface 10A to the silicon dioxide layer 11, thus providing the sensor chip 9 including the partition board 1 having the though-holes 4 and the frame 2. More specifically, the silicon dioxide layer 11 and the thin silicon layer 12 function as the partition board 1 while the silicon base 10 having the cavity 13 functions as the frame 2.

Particles which include organic compounds and float in the air are often absorbed on the upper surface 111A, on the lower surface 111B, and on the walls 4C of the through holes 4 of the partition board 1 of the sensor chip 9 provided by the above processes, and make the upper surface 111A and the lower surface 111B of the partition board 1 hydrophobic.

Then, the following process is performed to the sensor chip 9 produced by the processes shown in FIGS. 8 to 11 as to remove such organic compounds from the upper surface 111A, the lower surface 111B, and the walls 4C, i.e., the cell contact surface, of the partition board 1. The atomic ratio of carbon in the surface of the partition board should not be greater than 15 atomic percent of the composition of the surface of the partition board. Metals and ions can stay because they increase the hydrophilicity of the surface. The water contact angle D1 (See FIG. 7) should not be greater than 10 degrees to maintain hydrophilicity of the surface.

An oxidant is added into to concentrated sulfuric acid having a temperature controlled between 80° C. to 125° C., thus providing sulfuric acid solution, i.e., oxidizing solution. The oxidant may preferably be one selected from ammonium persulfate $(NH_4)_2S_2O_8$, nitric acid $HNO_3$, and ozone $O_3$. Ammonium persulfate, nitric acid, and ozone are supplied in the form of solid, liquid, and gas, respectively, thus being added to the concentrated sulfuric acid with their appropriate devices.

The following reaction occurs between ammonium persulfate and concentrated sulfuric acid and produces $H_2S_2O_3$:

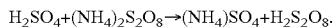

While the sensor chip 9 is immersed in the oxidizing solution the organic compounds adhered on the surfaces of the sensor chip 9 including the upper surface 111A, the lower surface 111B, and the wall 4C of the partition board 1 reacts with $H_2S_2O_8$ as follows:

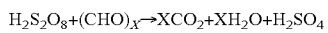

where $(CHO)_X$ is a CH group having a length of X. This reaction decomposes the organic compounds on the surfaces of the sensor chip 9.

Ammonium persulfate as the oxidant produces sulfuric acid $H_2SO_4$ as a byproduct in the above reaction. The reaction between concentrated sulfuric acid and ammonium persulfate as the oxidant occur continuously by the reaction of the CH groups with $H_2S_2O_8$, thus producing sulfuric acid as a final product. This reaction reduces the decomposition and consumption of sulfuric acid by an amount less than the amount of the reaction products, hence preventing deterioration of the sulfuric acid solution and providing the sensor chip 9 stably.

Then, the sensor chip 9 which has been immersed in the oxidizing solution is rinsed with double distilled water to remove remaining oxidizing solution, and then, is stored in double distilled water.

The chip sensor 9 may be immersed in an ammonium hydroxide solution after being immersed in the oxidizing solution. The ammonium hydroxide solution etches the surfaces of the silicon dioxide layers 11 and 18 at the surface of the partition board 1. The etching effectively removes organic compounds further from the surfaces of the partition board 1. This etching increases the smoothness of the surfaces of the partition board 1, thus providing further hydrophilicity. The partition board 1 may be preferably coated with silicon dioxide or a material containing silicon dioxide. Silicon dioxide has a small etching rate during being etched with the ammonium hydroxide solution, thus protecting the partition board 1 from over-etched. If silicon exposes at the surface of the partition board 1, the silicon is controlled to avoid over-etched with the ammonium hydroxide solution. If the partition board 1 is etched excessively, the surface has a small smoothness, thus having small hydrophilicity. The ammonium hydroxide solution may be replaced by an alkali water solution which contains at least one of ammonium, sodium hydroxide, potassium hydroxide, and lithium hydroxide.

The organic compounds have been removed from the surfaces by the above processes, and then, the sensor chip 9 is rinsed with double distilled water and is stored in double distilled water.

The sensor chip 9 may be immersed in a mixture of chloroform and methanol before being immersed in the oxidizing solution. This process effectively removes compounds that is soluble to organic solvent from the surfaces of the sensor chip 9, and allows the succeeding processes to be performed efficiently. After being immersed in the mixture of chloroform and methanol, the sensor chip 9 may be preferably rinsed with double distilled water. After being rinsed with double distilled water, the sensor chip 9 is immersed in the oxidizing solution.

Figure 12:
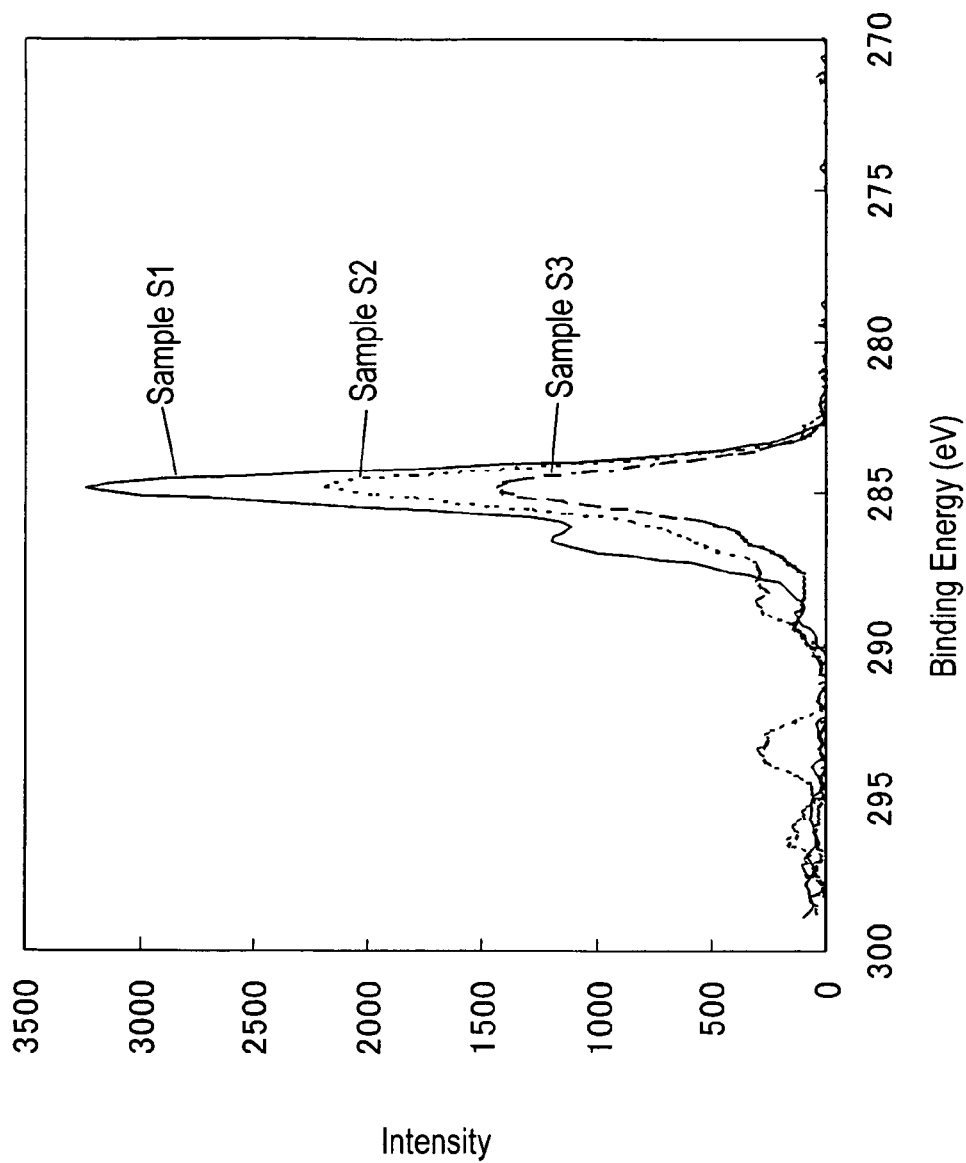
FIG. 12 shows an evaluation result of the cell electro-physiological sensor according to the embodiment.

The effects of the above processes that remove organic compounds and increase the hydrophilicity of the surface are shown in FIGS. 12 and 13. Samples S1, S2 and S3 are the sensor chips 9 and were all manufactured in the same way. Sample S1 was not treated with the oxidizing solution. Sample S2 was treated with the oxidizing solution and rinsed with double distilled water. Sample S3 was treated with the oxidizing solution, rinsed with double distilled water, and etched with ammonium hydroxide solution. FIG. 12 depicts the XPS spectra for samples S1, S2, and S3 that indicate the amount of elements on the surface of each sample.

FIG. 13 is a table summarizing the atomic ratios of top three elements found on the surface, namely, carbon, oxygen, and silicon, as well as the water contact angle D1 (See FIG. 7) of the surface of each sample. The water contact angle D1 indicates the hydrophilicity of the surfaces of the samples.

In sample S1, 18 atomic percent of the surface composition was carbon, and the contact angle D1 was 49.5 degrees. The sample S1 may not hold cell 8 tightly enough on the cell contact surface, the upper surface 111A, of the partition board 1.

In sample S2, 14 atomic percent of the surface composition was carbon, and its water contact angle D1 was 7.8 degrees, exhibiting that its hydrophilicity is much larger than that of the sample S1. The larger the hydrophilicity is, the more the strength (surface tension) of pulling the water at the surface is. This allows a solution to easily flow into the through-holes 4, and the cell 8 is accordingly sucked to the opening 4A of the through-hole 4 strongly. Although the water contact angle on the wall 4C of the through-hole 4 of the partition board 1 was not directly measured, the improvement of the hydrophilicity was shown by the fact that the oxidizing solution flowed easily into the through-hole 4. In sample S3, only 9 atomic percent of the surface composition was carbon and its water contact angle D1 was 3.1 degrees, showing that its hydrophilicity is yet larger than that of each of the sample S1 and S2.

Figure 14:
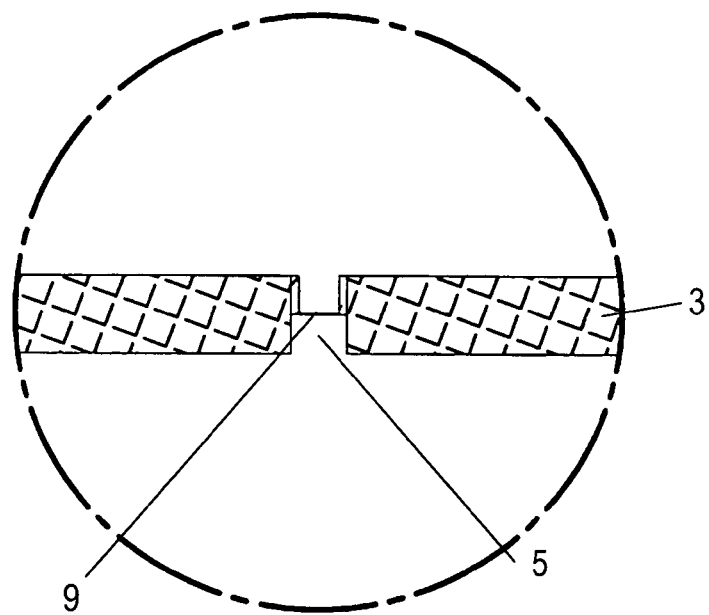
FIG. 14 is a cross sectional view of the cell electro-physiological sensor for illustrating a method of manufacturing the sensor according to the embodiment.

The sensor chip 9 that had been stored in the double distilled water after the surface treatment was taken out of the water, and the surface of the chip was dried partially, and then, is inserted into the through-hole 5 in the chip plate 3, as shown in FIG. 14.

Figure 15:
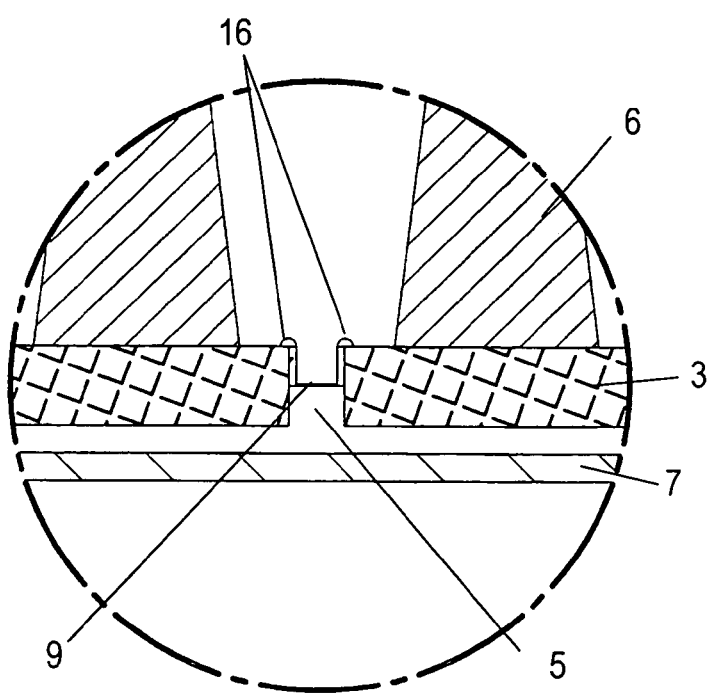
FIG. 15 is a cross sectional view of the cell electro-physiological sensor for illustrating the method of manufacturing the sensor according to the embodiment.

Then, as shown in FIG. 15, an adhesive 16 was applied to a portion of the sensor chip 9 in the through-hole 5 as to fill the gap between the sensor chip 9 and the chip plate 3 in the through-hole 5 with the adhesive 16. The adhesive 16 may preferably be ultraviolet curable for easy handling. Ultraviolet-curable adhesives do not require a heating process required for heat-curable adhesives, and can be cured within a short period of time. As a result, the partition board 1, in particular region around the through-holes 4, does not expose to the air for a long period of time, thus not reducing its hydrophilicity.

After the adhesive 16 was cured, the chip plate 3 having the sensor chips 9 installed therein was placed and sealed in a container filled with water or water vapor for storing the chip plate 3.

The above process allows the plate to be stored until its usage while the cell contact surfaces, the upper surface 111A, the lower surface 111B, and the wall 4C of the through-hole 4, of the partition board 1 expose to water or water vapor. This operation allows cell 8 to be sealed tightly at the though-hole 4 with very small current leakage, thus allowing a cell potential to be measured efficiently.

As described, the cell electro-physiological sensor 101 according to the embodiment holds cell 8 tightly at the opening 4A of the through-hole 4 in the partition board 1, and measured a cell potential with a very small current leakage. Consequently, the cell electro-physiological sensor 101 can be used in a screening device for examining chemical effects on the cell 8 and screening chemicals.

What is claimed is:

1. A cell electro-physiological sensor comprising:
   a sensor chip including a partition board having a first surface and a second surface opposite to the first surface of the partition board, the partition board having a through-hole provided therein, the through-hole having a first opening, a second opening, and a wall, the first opening of the through-hole opening to the first surface of the partition board, the second opening of the through-hole opening at the second surface of the partition board, the through-hole having substantially the same diameter as the through-hole extends from the first opening to the second opening;
   a first region provided on the first surface of the partition board, the first region contacting the first opening of the through-hole, the first region being arranged to hold cell suspension; and
   a second region provided on the second surface of the partition board, the second region contacting the second opening of the through-hole,
   wherein an atomic ratio of carbon at the first surface of the partition board is 9 atomic percent or greater and is not greater than 15 atomic percent of a composition of the first surface of the partition board.

2. The electro-physiological sensor according to claim 1, wherein an atomic ratio of carbon at the wall of the through-hole of the partition board is not greater than 15 atomic percent of a composition of the wall.

3. The cell electro-physiological sensor according to claim 1, wherein an atomic ratio of carbon at the second surface of the partition board is not greater than 15 atomic percent of a composition of the second surface.

4. The cell electro-physiological sensor according to claim 1, wherein a contact angle of a water drop on the first surface of the partition board is not greater than 10 degrees.

5. The cell electro-physiological sensor according to claim 4, wherein a contact angle of a water drop on the wall of the through-hole of the partition board is not greater than 10 degrees.

6. The cell electro-physiological sensor according to claim 4, wherein a contact angle of a water drop on the second surface of the partition board is not greater than 10 degrees.

7. The cell electro-physiological sensor according to claim 1, wherein the partition board includes a silicon dioxide layer at the first surface thereof.

8. The cell electro-physiological sensor according to claim 1, wherein the partition board includes a silicon dioxide layer at the second surface thereof.

9. The cell electro-physiological sensor according to claim 1, wherein the partition board includes a silicon dioxide layer at the wall of the through-hole.

10. The cell electro-physiological sensor according to claim 1, wherein the sensor chip is stored while the first surface, the second surface, and the through-hole of the partition board are filled with water.

11. A cell electro-physiological sensor comprising:
a chip plate having a first through-hole extending between an upper surface of the chip plate and a lower surface of the chip plate;
a sensor chip disposed in the first through-hole between the upper surface and the lower surface of the chip plate;
an electrode mounted on the upper surface of the chip plate and around the first through-hole;
the sensor chip including a partition board having a first surface and a second surface opposite to the first surface of the partition board, the partition board having a second through-hole provided therein, the second through-hole having a first opening, a second opening, and a wall, the first opening of the second through-hole opening to the first surface of the partition board, the second opening of the second through-hole opening at the second surface of the partition board, the second through-hole having substantially the same diameter as the second through-hole extends from the first opening to the second opening;
a first region provided on the first surface of the partition board, the first region contacting the first opening of the second through-hole, the first region being arranged to hold cell suspension; and
a second region provided on the second surface of the partition board, the second region contacting the second opening of the second through-hole,
wherein an atomic ratio of carbon at the first surface of the partition board is greater than zero and is not greater than 15 atomic percent of a composition of the first surface of the partition board, and
wherein an electric current is substantially prevented from leaking through the second through-hole to the second region.

12. The electro-physiological sensor according to claim 11, wherein an atomic ratio of carbon at the wall of the second through-hole of the partition board is not greater than 15 atomic percent of a composition of the wall.

13. The cell electro-physiological sensor according to claim 11, wherein an atomic ratio of carbon at the second surface of the partition board is not greater than 15 atomic percent of a composition of the second surface.

14. The cell electro-physiological sensor according to claim 11, wherein a contact angle of a water drop on the first surface of the partition board is not greater than 10 degrees.

15. The cell electro-physiological sensor according to claim 14, wherein a contact angle of a water drop on the wall of the second through-hole of the partition board is not greater than 10 degrees.

16. The cell electro-physiological sensor according to claim 14, wherein a contact angle of a water drop on the second surface of the partition board is not greater than 10 degrees.

17. The cell electro-physiological sensor according to claim 11, wherein the partition board includes a silicon dioxide layer at the first surface thereof.

18. The cell electro-physiological sensor according to claim 11, wherein the partition board includes a silicon dioxide layer at the second surface thereof.

19. The cell electro-physiological sensor according to claim 11, wherein the partition board includes a silicon dioxide layer at the wall of the through-hole.

20. The cell electro-physiological sensor according to claim 11, wherein the sensor chip is stored while the first surface, the second surface, and the second through-hole of the partition board are filled with water.

* * * * *